(12) United States Patent
Gudeman et al.

(10) Patent No.: US 11,197,688 B2
(45) Date of Patent: Dec. 14, 2021

(54) SURGICAL INSTRUMENT

(71) Applicants: Matthew S. Gudeman, Mundelein, IL (US); Mateusz Latawiec, Mundelein, IL (US); Matthew Rassi, Mundelein, IL (US)

(72) Inventors: Matthew S. Gudeman, Mundelein, IL (US); Mateusz Latawiec, Mundelein, IL (US); Matthew Rassi, Mundelein, IL (US)

(73) Assignee: JSTONE, INC., Mundelien (IL)

( * ) Notice: Subject to any disclaimer, the term of this patent is extended or adjusted under 35 U.S.C. 154(b) by 300 days.

(21) Appl. No.: 16/385,250

(22) Filed: Apr. 16, 2019

(65) Prior Publication Data

US 2019/0314047 A1    Oct. 17, 2019

Related U.S. Application Data

(60) Provisional application No. 62/658,713, filed on Apr. 17, 2018.

(51) Int. Cl.
*A61B 17/3201* (2006.01)
*A61B 17/32* (2006.01)
*A61B 17/29* (2006.01)

(52) U.S. Cl.
CPC .. *A61B 17/3201* (2013.01); *A61B 17/320016* (2013.01); *A61B 2017/2902* (2013.01); *A61B 2017/2945* (2013.01)

(58) Field of Classification Search
CPC ........ A61B 17/3201; A61B 17/320016; A61B 2017/2945; A61B 2017/2902; A61B 2017/2931; A61B 2017/00473; A61B 2017/2936
See application file for complete search history.

(56) References Cited

U.S. PATENT DOCUMENTS

| 5,722,988 A * | 3/1998 | Weisshaupt | A61B 17/29 606/205 |
| 2006/0161190 A1 * | 7/2006 | Gadberry | A61B 17/29 606/174 |
| 2011/0029010 A1 * | 2/2011 | Castro | A61B 17/29 606/206 |

* cited by examiner

*Primary Examiner* — Richard G Louis
(74) *Attorney, Agent, or Firm* — Justin Lampel

(57) ABSTRACT

A surgical instrument is provided, namely surgical scissors. The surgical instrument has a removable actuating rod which, in conjunction with the clevis and a tube, provides means for securing blades of the scissors. The tube prevents a removable pivot pin of the blades from becoming displaced from the clevis of the instrument. When the actuating rod is removed from the surgical instrument the pivot pin may be removed and, thus, the blades of the scissors may be removed for cleaning and/or replacement. The tube provides the tension and further constrains the scissor blades in a manner which results in the consistent and effective cutting performance of the scissors post assembly.

6 Claims, 9 Drawing Sheets

SURGICAL INSTRUMENT

REFERENCE TO RELATED APPLICATIONS

This application claims priority to U.S. Provisional Application No. 62/658,713, which is entitled "SURGICAL INSTRUMENT" which was filed on Apr. 17, 2018, the entire contents of which are incorporated by reference herein.

BACKGROUND OF THE INVENTION

A surgical instrument is provided, namely surgical scissors. The surgical instrument has a removable actuating rod which, in conjunction with the clevis and a tube, provides means for securing blades of the scissors. The tube prevents a removable pivot pin of the blades from becoming displaced from the clevis of the instrument. When the actuating rod is removed from the surgical instrument the pivot pin may be removed and, thus, the blades of the scissors may be removed for cleaning and/or replacement. The tube provides the tension and further constrains the scissor blades in a manner which results in the consistent and effective cutting performance of the scissors post assembly.

Numerous surgical instruments which utilize a clevis have been invented in the past. For example, U.S. Pat. No. 8,037,591 to Spivey discloses surgical scissors devices. The surgical scissors devices may comprise an end effector with first and second blade members. The first and second blade members may respectively comprise proximally positioned cams and distally positioned blade ends. Also, the first and second blade members may be coupled at a pivot point by a fastener held in tension along its longitudinal axis by the blade members. A reciprocating shuttle may comprise at least one pin positioned within slots defined by the respective cams of the blade members. Distally-directed motion of the shuttle may cause the first and second blade members to open and proximally-directed motion of the shuttle may cause the first and second blade members to close. Methods and apparatuses for forming the surgical scissors device are also disclosed Further, U.S. Pat. No. 6,562,035 to Levin discloses insulated surgical scissors having a cauterizing tip that permits a surgeon the ability to mechanically cut tissue that is purchased between the cutting blades of the scissors and to apply a cauterization current to a precise portion of the seized tissue, thereby minimizing inadvertent burning of surrounding tissue. Both monopolar and bipolar configurations of the insulated surgical scissors are provided.

Still further, U.S. Pat. No. 5,358,508 to Cobb discloses a laparoscopic instrument assembly having a removable tip attachable to an actuator, the actuator being provided with an actuator tube disposed for axial movement within a tubular sheath. The removable tip has a pair of blades forming a scissors which are moved between an open position and a closed position by axial movement of a tip tube disposed within a tubular tip casing structure. The tip tube is threaded to the actuator tube and the tip casing structure is threaded to the actuator tubular sheath, and a pair of thumb and finger grips serve to move the actuator tube within the tubular sheath.

However, these patents fail to provide a surgical instrument as defined in the present application. More specifically, these patents fail to provide a surgical instrument which utilizes a tube assembly to secure a removable pin of blades of scissors while also constraining the scissor blades in a manner which results in a consistent and effective cutting action post assembly.

SUMMARY OF THE INVENTION

A surgical instrument is provided, namely surgical scissors. The surgical instrument has a removable actuating rod which, in conjunction with the clevis and a tube, provides means for securing blades of the scissors. The tube prevents a removable pivot pin of the blades from becoming displaced from the clevis of the instrument. When the actuating rod is removed from the surgical instrument the pivot pin may be removed and, thus, the blades of the scissors may be removed for cleaning and/or replacement. The tube provides the tension and further constrains the scissor blades in a manner which results in the consistent and effective cutting performance of the scissors post assembly.

An advantage of the present surgical instrument is that the present surgical instrument reduces the costs associated with laparoscopic instruments by allowing a user to be able to quickly and easily replace the blades of laparoscopic scissors in the hospital (or other location) whereas previously, the entire laparoscopic device would need to be sent out for repair and/or replacement of parts after each use.

Another advantage of the present surgical instrument is that, when assembled the only components not insulated are the blades of the scissors.

Yet another advantage of the present surgical instrument is that the tube assembly may constrain a floating clevis assembly which therein allows for the use of a floating pivot pin as opposed to a pre-set screw or rivet with the result of effective scissors performance post assembly.

And another advantage of the present surgical instrument is that the clevis of the present surgical instrument is concealed and insulated when the instrument is fully assembled.

Still another advantage of the present surgical instrument is that the components, such as the clevis, rod and main tube of the surgical instrument may be reusable.

For a more complete understanding of the above listed features and advantages of the present surgical instrument, reference should be made to the following detailed description of the preferred embodiments and to the accompanying drawings.

DETAILED DESCRIPTION OF THE PREFERRED EMBODIMENTS

A surgical instrument is provided, namely surgical scissors. The surgical instrument has a removable actuating rod which, in conjunction with the clevis and a tube, provides means for securing blades of the scissors. The tube prevents a removable pivot pin of the blades from becoming displaced from the clevis of the instrument. When the actuating rod is removed from the surgical instrument the pivot pin may be removed and, thus, the blades of the scissors may be removed for cleaning and/or replacement. The tube provides the tension and further constrains the scissor blades in a manner which results in the consistent and effective cutting performance of the scissors post assembly.

Figure 14:
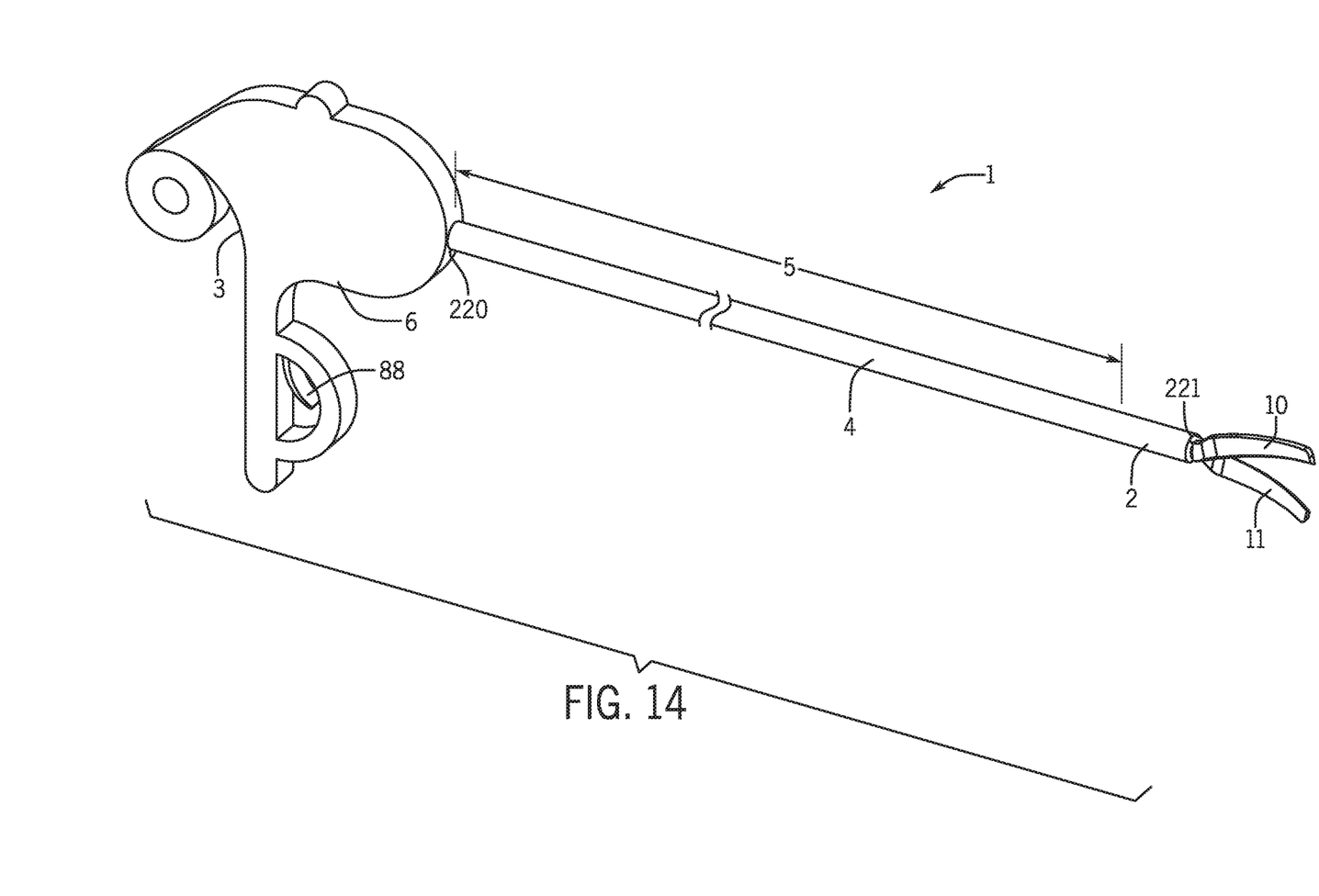
FIG. 14 illustrates a perspective view of the fully assembled laparoscopic scissors.
Figure 15:
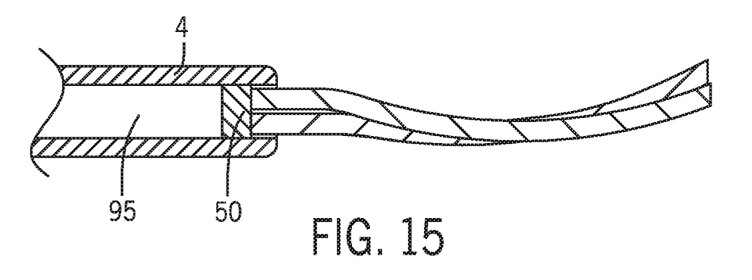
FIG. 15 illustrates a cross-sectional view of the pin located in the clevis wherein the pin is secured by the inner walls of the main tube.
Figure 16:
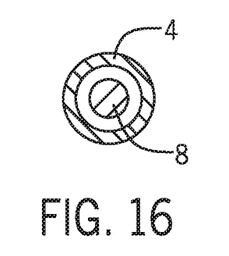
FIG. 16 illustrates a cross-sectional view of the extended rod located in the main tube.
Figure 17:
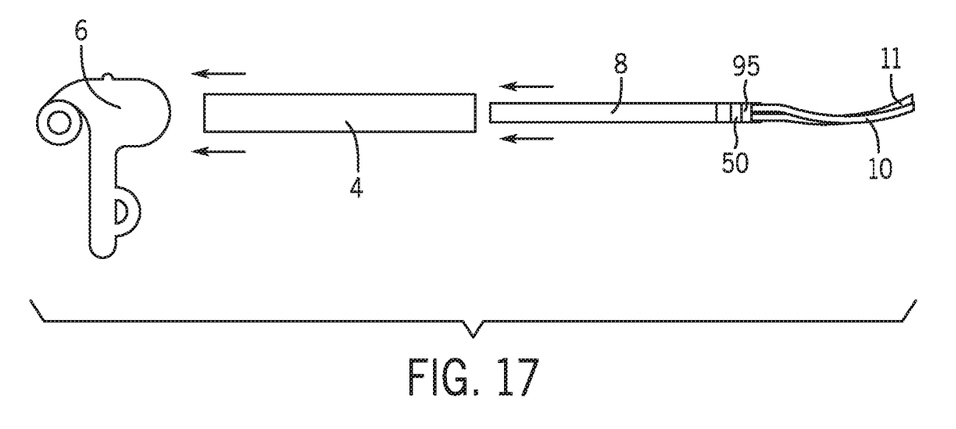
FIG. 17 illustrates the main tube in the process of being inserted over the extended rod wherein the clevis and blades are already secured to the extended rod.

Referring first to FIG. 14, in an embodiment, a surgical instrument 1 is provided. The surgical instrument 1 may have a first end 2, a second end 3 and a main tube 4 having a first end 220, a second end 221 and a length 5. Preferably, the main tube 4 is generally cylindrically-shaped. The first end 2 of the surgical instrument 1 may have a first blade 10 and a second blade 11 which, in an embodiment, form surgical scissors. The second end 3 of the surgical instrument 1 may have a handle portion 6 having a trigger 88 which allows a user to activate the blades 10, 11 of the scissors portion of the instrument 1. Preferably, the laparoscopic instrument 1 is made of various durable materials such as, for example, metal, plastic and rubber. In an embodiment, the blades 10, 11 may be replaced with, for example, grasping mechanisms such as tweezers or other surgical implements.

Figure 1:
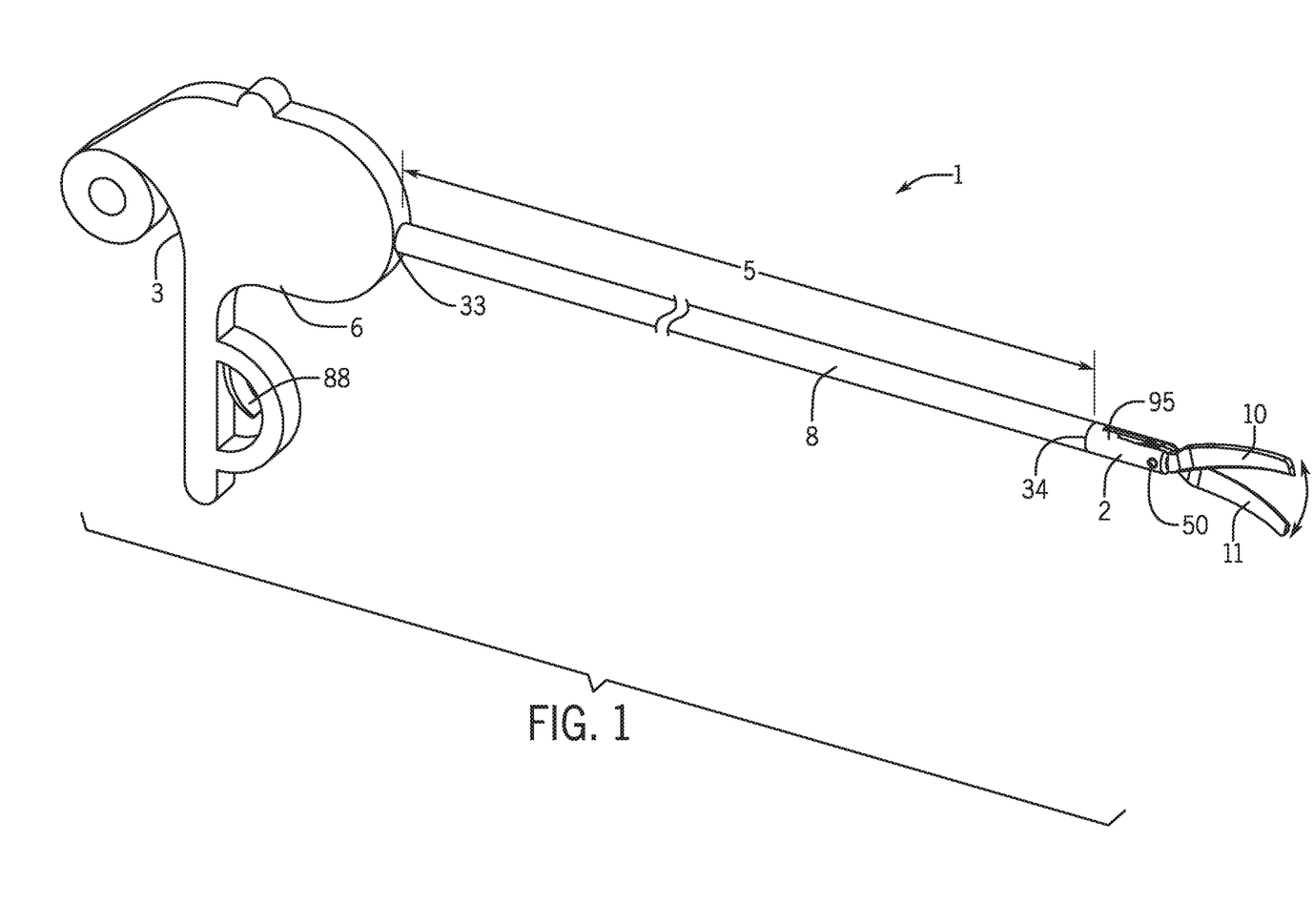
FIG. 1 illustrates a perspective view of the laparoscopic scissors wherein the main tube is removed and the clevis is visible.
Figure 2:
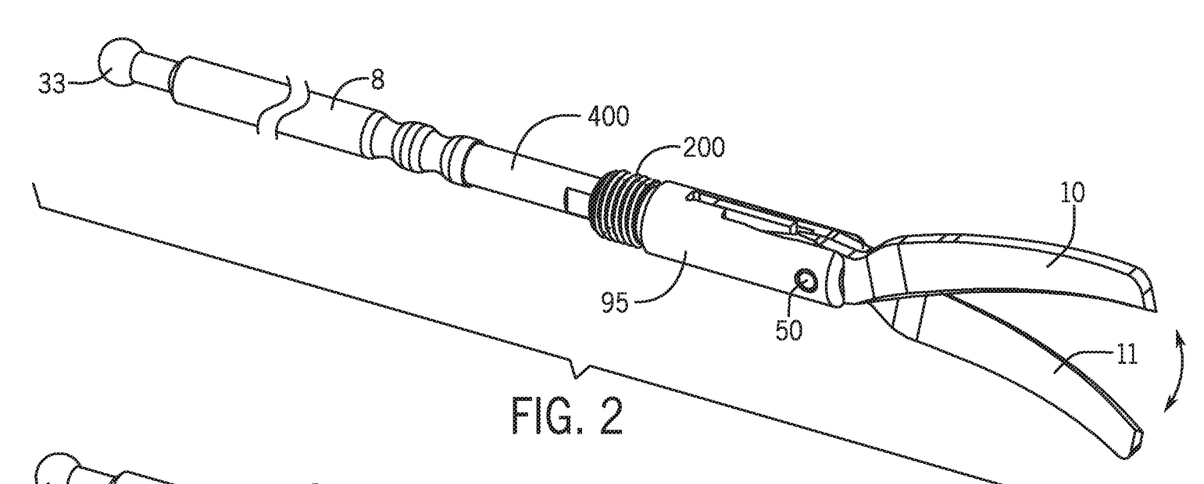
FIG. 2 illustrates a perspective view of the first end of the laparoscopic scissors wherein the main tube is removed and the clevis visible and wherein the blades are in the open position.
Figure 3:
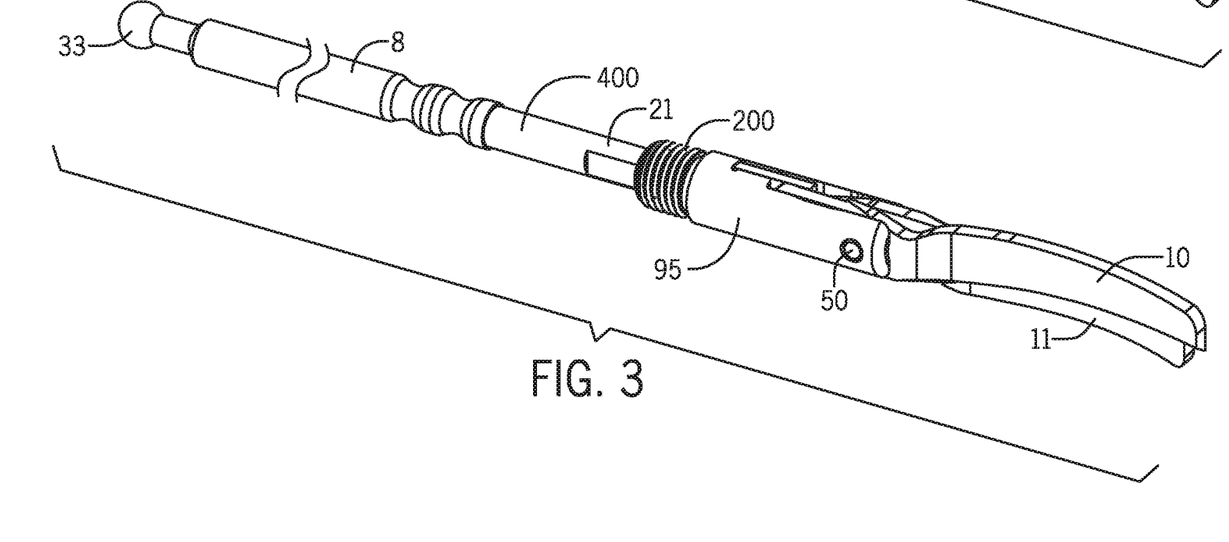
FIG. 3 illustrates a perspective view of the first end of the laparoscopic scissors wherein the main tube is removed and the clevis is visible and wherein the blades are in the closed position.

In an embodiment, the main tube 4 may be removable from the instrument 1 (as shown in FIG. 1) so that the instrument 1 and its components may be cleaned, sterilized and/or replaced; especially the blades 10, 11. Further, the main tube 4 may have an interior 7 (FIG. 13) in which an extended rod 8 may be located. The extended rod 8 may have a first end 33 and a second end 34. In an embodiment, the first end 33 of the extended rod 8 may be connected to the handle 6 portion of the instrument 1 while the second end 34 of the extended rod 8 may be connected to the main tube 4 (as discussed below) which secures and constrains the first blade 10, the second blade 11, a clevis 95 (FIG. 6) and a pivot pin 50. In an embodiment, the first blade 10 and the second blade 11 may rotate with respect to each other and together, may form scissors which are used in surgery. More specifically, the first blade 10 and the second blade 11 may rotate with respect to each other at the pivot pin 50 (FIG. 2) located within the clevis 95.

Figure 13:
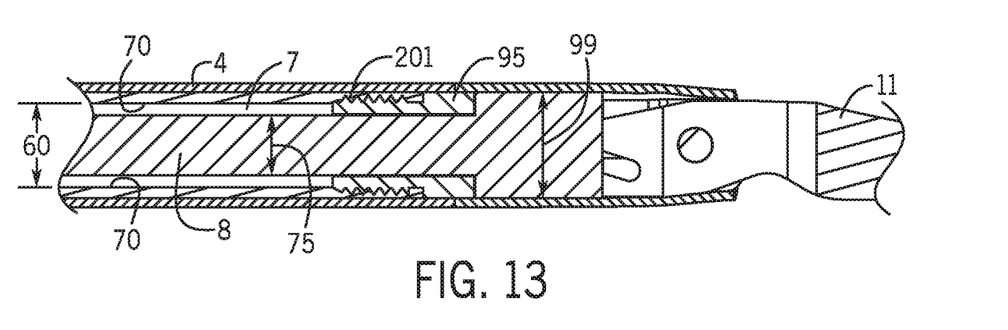
FIG. 13 illustrates a cross-sectional view of the first end of the laparoscopic instrument wherein the main tube is in place over the clevis and wherein the blades are therein secured within the instrument.

In an embodiment, the interior 7 of the main tube 4 may have a diameter 60 (FIG. 13) defined by the distance between the interior facing walls 70 of the main tube 4. More specifically, the diameter 60 may be defined as the interior diameter of the main tube 4 at a specific location within the main tube 4. As shown in FIG. 13, the diameter 60 of the main tube 4 may be different at the second end 221 of the main tube 4 than the remainder of the main tube 4. In particular, the diameter 60 at the second end 221 of the main tube 4 may be greater than the diameter 60 of the rest of the main tube 4. This allows for the clevis 95 to be inserted into place at the second end 221 of the main tube 4. In an embodiment, the extended rod 8 may also have a width 75 and the clevis 95 may have a width 99. The width 99 of the clevis 95 may be slightly smaller than the diameter of the interior of the main tube 4 at the second end 221 of the main tube 4 so that the clevis 95 is tightly secured within the interior 7 of the main tube 4 at the second end 221 of the main tube 4.

Figure 6:
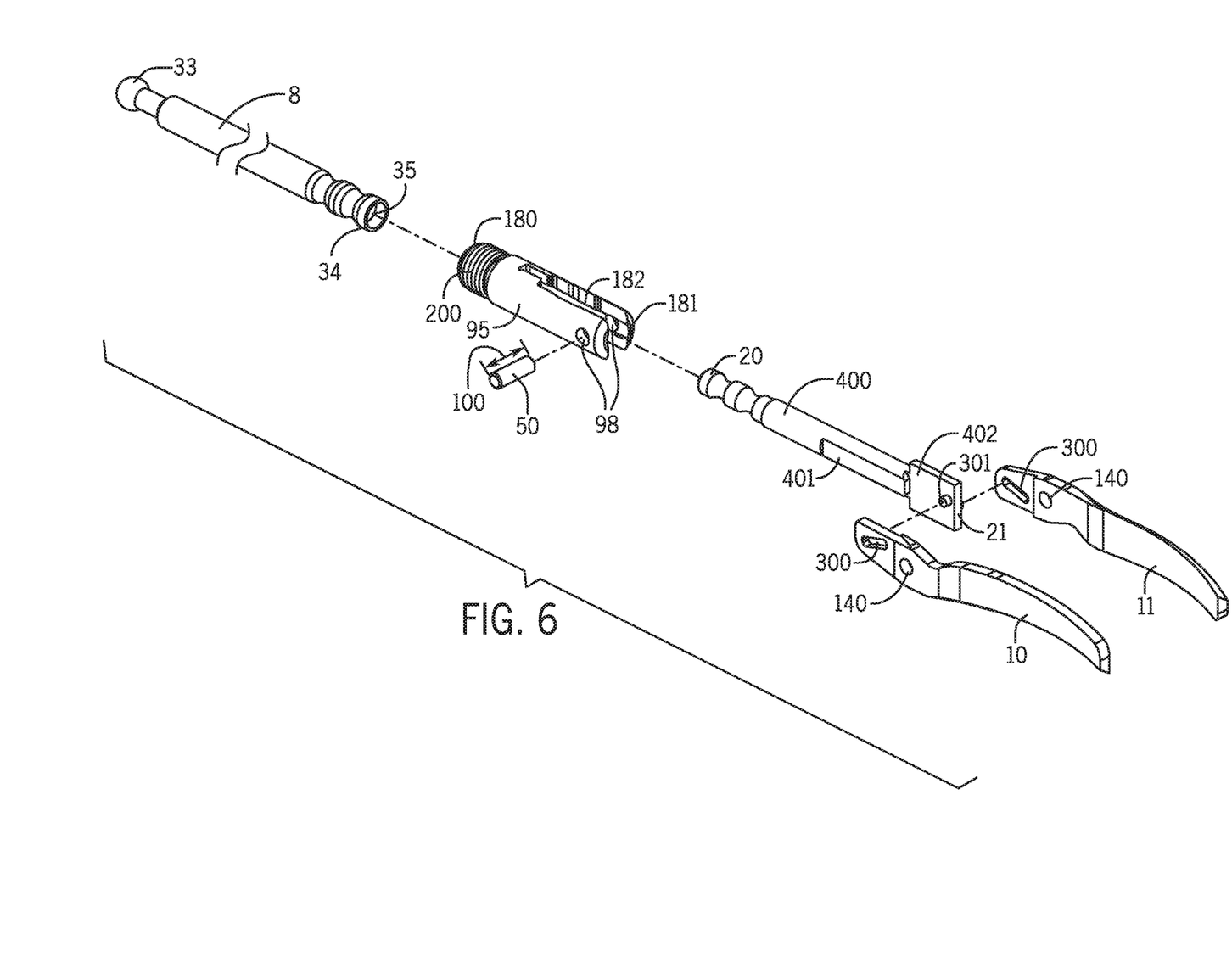
FIG. 6 illustrates an exploded view of the first end of the laparoscopic scissors wherein the main tube is removed.
Figure 7:
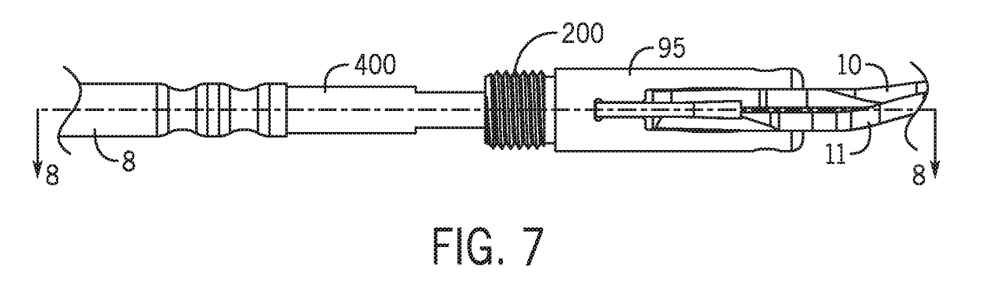
FIG. 7 illustrates a top view of the first end of the laparoscopic scissors wherein the main tube is removed and wherein the clevis is visible.
Figure 8:
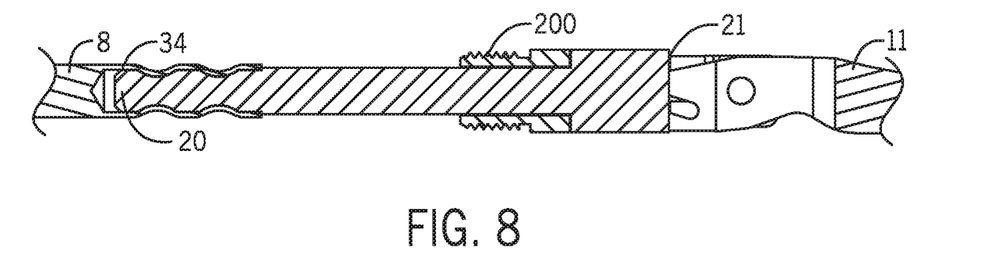
FIG. 8 illustrates a cross-sectional side view of the first end of the laparoscopic scissors wherein the main tube is removed.
Figure 9:
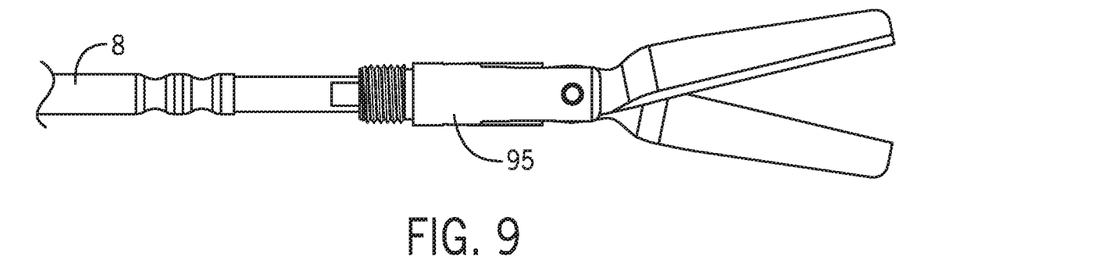
FIG. 9 illustrates a side view of the first end of the laparoscopic scissors wherein the main tube is removed and wherein the blades are in the open position.
Figure 10:
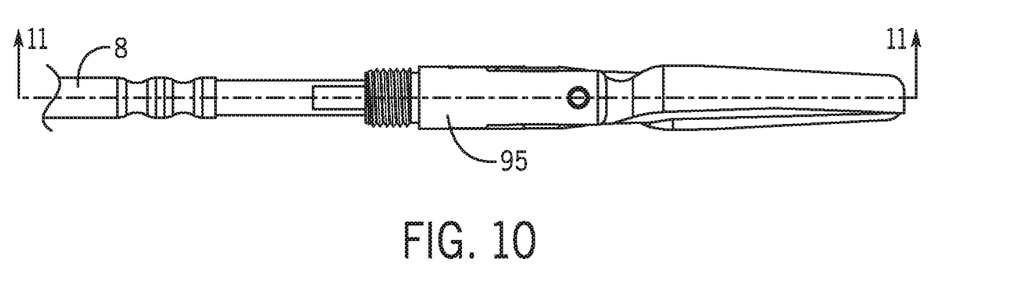
FIG. 10 illustrates a side view of the first end of the laparoscopic scissors wherein the main tube is removed and wherein the blades are in the closed position.
Figure 11:
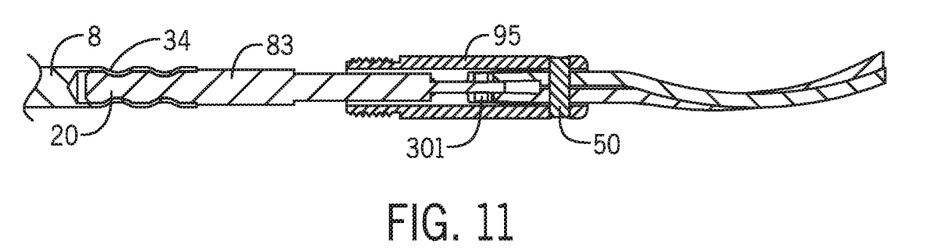
FIG. 11 illustrates a cross-sectional top view of the first end of the laparoscopic scissors in an embodiment wherein the main tube is removed and wherein the blades are curved.
Figure 12:
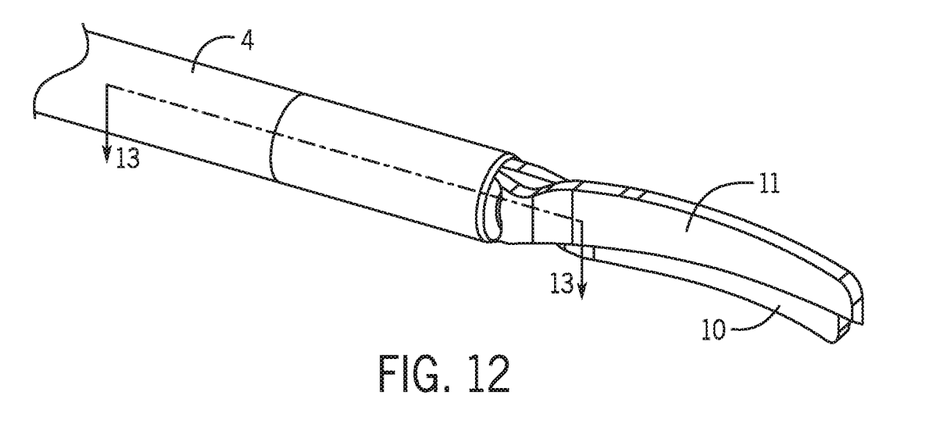
FIG. 12 illustrates a perspective view of the first end of the laparoscopic scissors wherein the main tube is secured over the clevis and the blades therefore cannot become dislocated from the instrument (the "usable" condition).

In an embodiment, the pivot pin 50 may be generally cylindrical and may have a length 100 (FIG. 6). The length 100 of the pivot pin 50 may be substantially similar to the diameter 60 of the interior 7 of the removable main tube 4 (at the clevis 95 location at the second end 221 of the main tube 4) and substantially similar or identical to the width 99 of the clevis 95 so that the pivot pin 50 snugly fits within the interior 7 of the main tube 4 at the second end 221 of the main tube 4. In particular, to assemble the instrument 1, the first blade 10 and the second blade 11 may be placed adjacent to the clevis 95. The pivot pin 50 may then be inserted through openings 140 (FIG. 6) in both the first blade 10 and the second blade 11 and further the clevis 95 so that the pivot pin 50 secures all three units together. The main tube 4 is then inserted over the extended rod 8.

The three units (the clevis and two blades) are temporarily secured by the pivot pin 50. The clevis 95 is also secured to a securing bar 400 which is therein attached to the extended rod 8. The clevis 95 is inserted into the main tube 4 so that a controlled clearance with the interior side walls 70 of the main tube 4 keeps the three units (the clevis and first and the second blade) together. Thus, without soldering or welding the pivot pin 50 or otherwise applying a screw or rivet, the pivot pin 50 may simply be inserted through the three units and may remain there as the result of the interior wall 70 of the main tube 4 acting as a restraining mechanism without any additional securing element.

More specifically, the pivot pin 50 is first inserted into the openings 140 of the blades 10, 11 and also the opening 98 of the clevis 95 and then the main tube 4 is then slid over the extended rod 8 and the clevis 95 by sliding the main tube 4 over the first end 33 of the extended rod 8 toward the second end 34 of the extended rod 8. Once the main tube 4 is secured over the extended rod 8 and the main tube 4 is screwed into place by the corresponding threaded members 200, 201 the first end 220 of the main tube 4 and the first end 33 of the extended rod 8 are then secured to the handle portion 6. Once the main tube 4 is secured in place, the pivot pin 50 may remain in place during use of the device by being restricted by the interior walls 70 of the main tube 4. Prior art clevis devices utilize screws or permanent rivets to attach the three units and to control the effectiveness of the scissors.

To separate the first blade 10 and the second blade 11 from the clevis 95 in the present device 1 a user simply removes the main tube 4 from the extended rod 8 (by unscrewing the same) and then a user applies a force (though a needle or other instrument) to easily push the pivot pin 50 out of the openings 140 of the first blade 10, the second blade 11 and the clevis 95. Prior art instruments required extensive work to remove the pin securing the first blade and the second blade to a clevis, thus rendering the instrument unusable for an extended period of time.

Figure 4:
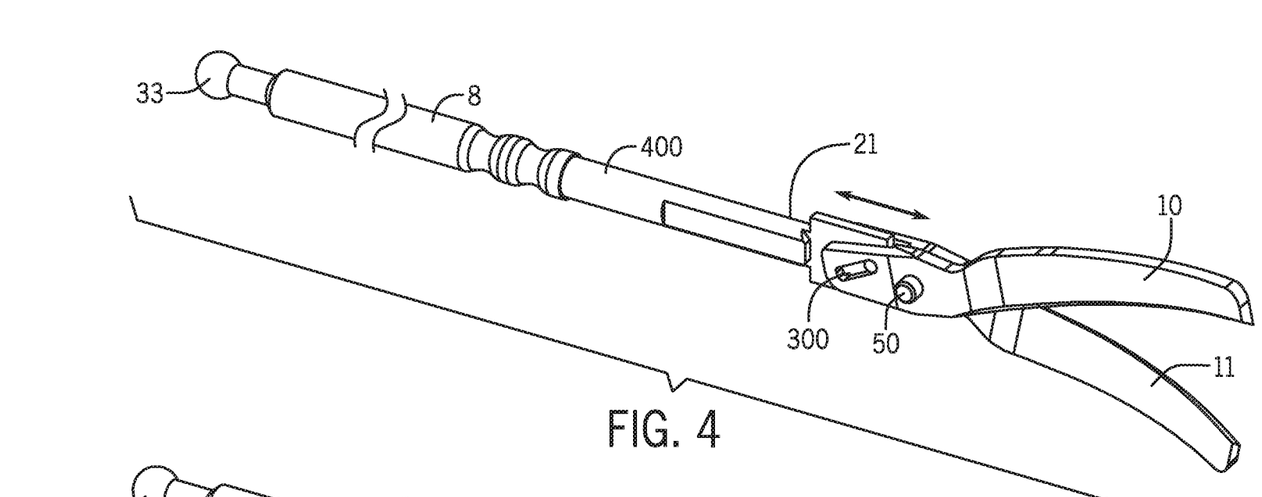
FIG. 4 illustrates a perspective view of the blades and securing bar of the first end of the laparoscopic instrument wherein the main tube and clevis are removed and wherein the blades are in the open positon.
Figure 5:
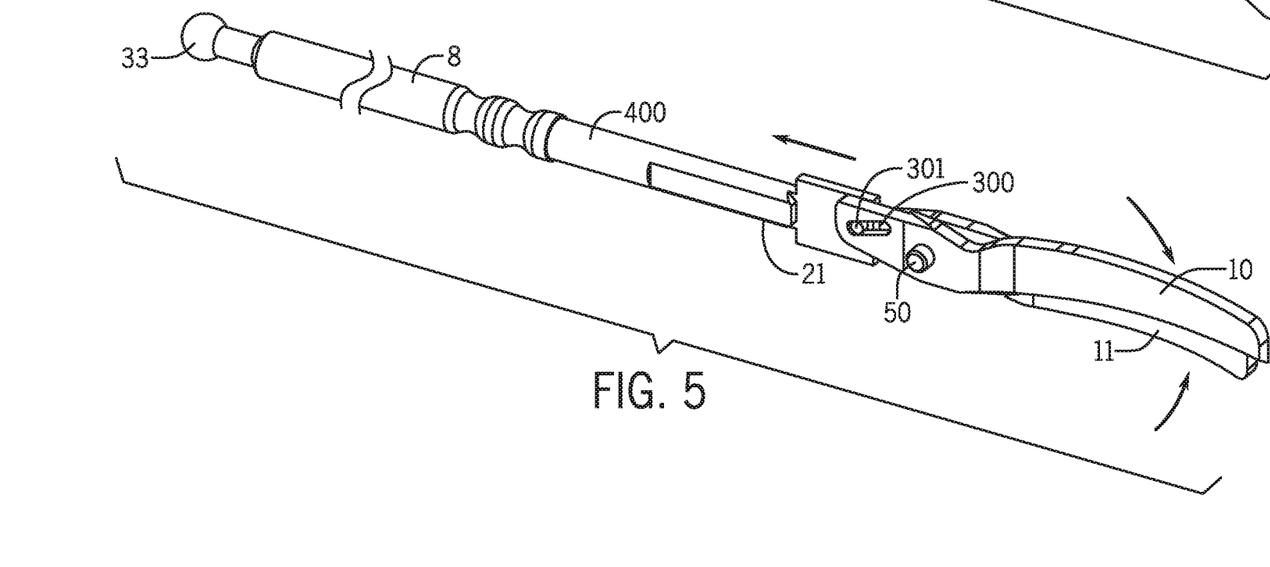
FIG. 5 illustrates a perspective view of the blades and securing bar of the first end of the laparoscopic instrument wherein the main tube and clevis are removed and wherein the blades are in the closed position.

In an embodiment, as illustrated in FIG. 6, the clevis 95 may have a first end 180 and a second end 181. In this embodiment, the second end 181 may have an opening slit 182 which receives the pivot pin 50 that connects the first blade 10 to the second blade 11. As stated above, the extended rod 8 may be connected to the securing bar 400, which in turn, connects to the clevis 95 which holds first blade 10 and the second blade 11 for the purpose of actuating blades 10, 11 as is illustrated in FIGS. 4 and 5.

In an embodiment, a threaded member 200 may be located at the first end 180 of the clevis 95. The threaded member 200 correspondingly locks into a second threaded member 201 (FIG. 13) located within the interior wall 70 of the main tube 4 near the second end 221 of the main tube 4 (near the blades 10, 11).

In an embodiment, the securing bar 400 of the device 1 may have a first end 20 and a second end 21. The first end 20 of the securing bar 400 may have a ball which is received within a spherical opening 35 of the second end 34 of the extended rod 8 and wherein the spherical opening 35 secures the securing bar 400 when it receives the ball of the securing bar 400. In an embodiment, the spherical opening 35 acts as a ball-joint to secure the first end 20 of the securing bar 400.

A slot 300 (FIG. 6) located on both the first blade 10 and the second blade 11 may receive a pin 301 located on a securing bar 400. In particular, the pin 301 may be located on a generally flat section 402 of the securing bar 400. In an embodiment, the pin 301 may be located on both sides of the generally flat section 402. In an embodiment, the pin 301 may be stationary with respect to the generally flat surface 402. The slot 300 of the first blade 10 and the slot 300 of the second blade 11 may be located in a non-parallel manner. In particular, as illustrated in FIG. 6, the first slot 300 and second slot 300 may be located at different angles so that when the extended rod 8 is moved forward or backward the slots 300 may move around the pin 301 and therein open or close the blades 10, 11 of the scissors. A second generally flat surface 401 on the securing bar 400 may allow for decreased overall weight of the apparatus 1.

Although embodiments of the present invention are shown and described therein, it should be understood that various changes and modifications to the presently preferred embodiments will be apparent to those skilled in the art. Such changes and modifications may be made without departing from the spirit and scope of the present invention and without diminishing its attendant advantages. It is, therefore, intended that such changes and modifications be covered by the present application.

The invention claimed is:

1. A surgical instrument comprising:
   a housing having first end and a second end;
   a movable surgical implement located at the first end wherein the movable surgical implement has a first unit and a second unit and wherein the first unit and the second unit each have an opening;
   a handle portion located at the second end;
   a tube having a hollow interior having a cylindrical wall located between the handle portion and the movable surgical implement wherein the interior of the tube has a diameter;
   a clevis located within the tube wherein the clevis has an opening which receives a pin;
   wherein the pin passes through the clevis and through the opening of the first unit and the opening of the second unit;
   a securing bar located within the interior of the tube wherein the securing bar has a first end and a second end and wherein the second end of the securing bar is secured to the clevis;
   an extended rod located within the interior of the tube wherein the extended rod has a first end and a second end and wherein the second of the extended rod is capable of securing the securing bar; and
   an opening at the second end of the extended rod wherein the opening of the second end of the extended rod receives the first end of the securing bar and secures the first end of the securing bar.

2. A surgical instrument of claim 1 wherein the opening at the second end of the extended rod is a ball joint.

3. A surgical instrument comprising:
   a housing having first end and a second end;
   a movable surgical implement located at the first end wherein the movable surgical implement has a first unit and a second unit and wherein the first unit and the second unit each have an opening;
   a handle portion located at the second end;
   a tube having a hollow interior having a cylindrical wall located between the handle portion and the movable surgical implement wherein the interior of the tube has a diameter;
   a clevis located within the tube wherein the clevis has an opening which receives a pin;
   wherein the pin passes through the clevis and through the opening of the first unit and the opening of the second unit;
   a securing bar located within the interior of the tube wherein the securing bar has a first end and a second end and wherein the second end of the securing bar is secured to the clevis;
   wherein the second end of the securing bar is flat and wherein the first end of the securing bar is cylindrical; and
   a pin located on the flat surface of the second end of the securing bar wherein the pin is stationary with respect to the flat surface and wherein the pin is received by a slot of the first unit and a slot of the second unit of the surgical implement.

4. A surgical instrument comprising:
   a housing having first end and a second end;
   a movable surgical implement located at the first end wherein the movable surgical implement has a first unit and a second unit and wherein the first unit and the second unit each have an opening;

a handle portion located at the second end;

a tube having a hollow interior having a cylindrical wall located between the handle portion and the movable surgical implement wherein the interior of the tube has a diameter;

a clevis located within the tube wherein the clevis has an opening which receives a pin; and wherein the pin passes through the clevis and through the opening of the first unit and the opening of the second unit;

wherein the pin has a length and wherein the pin is cylindrical having a uniform diameter and wherein the length of the pin is equal to or slightly smaller than the diameter of the tube at a location within the tube and wherein the pin is only prevented from exiting the opening of the first unit, the opening of the second unit or the opening of the clevis as a result of being held into place by the cylindrical wall of the interior of the tube;

a securing bar located within the interior of the tube wherein the securing bar has a first end and a second end and wherein the second end of the securing bar is secured to the clevis;

an extended rod located within the interior of the tube wherein the extended rod has a first end and a second end and wherein the second of the extended rod is capable of securing the securing bar; and an opening at the second end of the extended rod wherein the opening of the second end of the extended rod receives the first end of the securing bar and secures the first end of the securing bar.

5. The surgical instrument of claim 4 wherein the opening at the second end of the extended rod is a ball joint.

6. A surgical instrument comprising:

a housing having first end and a second end;

a movable surgical implement located at the first end wherein the movable surgical implement has a first unit and a second unit and wherein the first unit and the second unit each have an opening;

a handle portion located at the second end;

a tube having a hollow interior having a cylindrical wall located between the handle portion and the movable surgical implement wherein the interior of the tube has a diameter;

a clevis located within the tube wherein the clevis has an opening which receives a pin; and wherein the pin passes through the clevis and through the opening of the first unit and the opening of the second unit;

wherein the pin has a length and wherein the pin is cylindrical having a uniform diameter and wherein the length of the pin is equal to or slightly smaller than the diameter of the tube at a location within the tube and wherein the pin is only prevented from exiting the opening of the first unit, the opening of the second unit or the opening of the clevis as a result of being held into place by the cylindrical wall of the interior of the tube;

a securing bar located within the interior of the tube wherein the securing bar has a first end and a second end and wherein the second end of the securing bar is secured to the clevis;

wherein the second end of the securing bar is flat and wherein the first end of the securing bar is cylindrical; and a pin located on the flat surface of the second end of the securing bar wherein the pin is stationary with respect to the flat surface and wherein the pin is received by a slot of the first unit and a slot of the second unit of the surgical implement.

\* \* \* \* \*